(12) United States Patent
Bates et al.

(10) Patent No.: US 9,078,977 B2
(45) Date of Patent: Jul. 14, 2015

(54) DUAL SHIELDED SYRINGE

(71) Applicant: Becton, Dickinson and Company, Franklin Lakes, NJ (US)

(72) Inventors: James Bates, Sparta, NJ (US); Peter Skutnik, Midland Park, NJ (US); Amit Limaye, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/041,040

(22) Filed: Sep. 30, 2013

(65) Prior Publication Data

US 2015/0094666 A1 Apr. 2, 2015

(51) Int. Cl.
*A61M 5/32* (2006.01)
*A61M 5/178* (2006.01)

(52) U.S. Cl.
CPC ............ *A61M 5/3202* (2013.01); *A61M 5/1782* (2013.01); *A61M 5/326* (2013.01); *A61M 5/3257* (2013.01); *A61M 2005/3247* (2013.01); *A61M 2005/3267* (2013.01)

(58) Field of Classification Search
CPC ............ A61M 2005/3254; A61M 2005/3247; A61M 2005/3267; A61M 2005/3268; A61M 5/326; A61M 5/3271; A61M 25/0631; A61M 5/1782
USPC .......................................... 604/192, 197, 198
See application file for complete search history.

(56) References Cited

U.S. PATENT DOCUMENTS

| | | | |
|---|---|---|---|
| 5,010,486 A | 4/1991 | Suzuki et al. | |
| 5,382,241 A | 1/1995 | Choudhury et al. | |
| 5,466,223 A | 11/1995 | Bressler et al. | |
| 5,667,494 A * | 9/1997 | van den Haak | 604/195 |
| 6,183,440 B1 | 2/2001 | Bell | |
| 6,632,198 B2 | 10/2003 | Caizza | |
| 6,780,169 B2 | 8/2004 | Crawford | |
| 7,101,351 B2 | 9/2006 | Crawford et al. | |
| 7,651,512 B2 | 1/2010 | Chelak et al. | |
| 8,062,252 B2 | 11/2011 | Alheidt et al. | |
| 2002/0151853 A1 | 10/2002 | Crawford | |
| 2005/0020985 A1* | 1/2005 | Doyle | 604/192 |
| 2010/0137810 A1* | 6/2010 | Chandrasekaran et al. | 604/198 |
| 2011/0160701 A1* | 6/2011 | Wyatt et al. | 604/519 |
| 2011/0257603 A1* | 10/2011 | Ruan et al. | 604/198 |
| 2012/0010573 A1 | 1/2012 | Lundquist | |

FOREIGN PATENT DOCUMENTS

WO 2011095488 A1 8/2011

* cited by examiner

*Primary Examiner* — Nicholas Lucchesi
*Assistant Examiner* — Anh Bui
(74) *Attorney, Agent, or Firm* — Roylance, Abrams, Berdo & Goodman, L.L.P.

(57) ABSTRACT

A dual shield mechanism provides passive protection of a syringe cannula. The automatic shield system may be used with a re-fillable syringe, and may be adapted for filling the syringe from a vial using a novel vial adapter without triggering the passive shielding mechanism.

7 Claims, 8 Drawing Sheets

DUAL SHIELDED SYRINGE

BACKGROUND OF THE INVENTION

1. Field of the Invention

The invention is in the field of re-fillable syringes for medication delivery and in particular is directed to an apparatus for automatically shielding a re-fillable syringe.

2. Description of the Related Art

The prior art teaches various safety shield systems adapted for use with a medication pen. Examples of passive shielding systems include U.S. Patent Application Publication Nos. 2011/0288491 and 2011/0257603, which are incorporated by reference. The needle assemblies disclosed in these publications include a patient-side needle for administering the injection, and a proximal side needle which extends into the medication compartment of the medication pen. In embodiments, the needle assembly includes a passive dual-shield for the patient end cannula which provides for passive protection of the cannula before and after use, as well as a passively activated shield for covering the proximal side needle to prevent accidental needle stick when the needle assembly is removed from the medication pen.

A similar passive shielding system is not available for a refillable syringe, which is delivered empty to the user and which must be filled from a vial. The shielded syringe designs that do exist rely on user manipulation, such as a hinged cover connected at the base of the needle which the user folds over the needle after use, or a linearly actuated shield which is pushed with the thumb or opposite hand after injection is complete. U.S. Pat. No. 7,101,351 to Crawford, et al., for example, which is incorporated by reference, teaches a shield for a syringe activated by distal movement of the syringe plunger after an injection is administered.

A passive two-shielded design has not heretofore been adapted for use with a refillable syringe. Thus, an object of the invention is to provide a dual-shielded design for use with a syringe.

A further object of the invention is to provide a passively shielded syringe with a vial adapter to permit filling the syringe from a vial without activating the passive shield system.

SUMMARY OF THE INVENTION

In one aspect, the invention is a dual shielded re-fillable syringe, comprising: a tubular syringe body having a distal end, a proximal end, and features on the distal end adapted to engage a shield assembly. The shield assembly attached to the distal end of the syringe body comprises: (1) a hub, having features on a proximal end thereof for engaging the syringe body, (2) a needle fixed to the hub having a distal end extending from the hub and a proximal end in the interior of the hub which does not extend from the hub, (3) an inner shield having a tubular body at least partially encircling the needle, (4) an outer shield radially outward of the inner shield, having a tubular body and having an opening which receives the distal end of the inner shield, (5) a spring disposed to urge the inner shield distally through the opening in the outer shield towards the distal end of the needle, and (6) an outer sleeve at least partially encircling the inner and outer shields. A releasable retaining feature retains the inner shield in an initial position such that a predetermined extent of proximal movement of the outer shield relative to the hub and into the outer sleeve during an injection releases the inner shield under bias of the spring to urge the inner shield through the opening in the outer shield to a position covering the distal end of the needle.

Conventional syringe designs are typically either "integral," meaning that the syringe body is molded as one piece, or "snap-fit," meaning that the hub component is molded separately from the syringe body and pre-assembled before being delivered to the user. The dual shield assembly according to the present invention may be incorporated with either type of syringe, either by providing a shield assembly which is snap fit into the syringe barrel, or adhering or otherwise attaching the needle assembly onto the distal end of the syringe body.

Alternatively, a shield assembly as described above is configured with features on the proximal end for removable attachment to the syringe body, such as by a tapered luer connection, which may be a luer slip connection, threaded luer lock connection, or luer snap connection.

In another aspect of the invention, a vial adapter may be used for filling the syringe, preventing the automated shield from being triggered prior to administering an injection. The vial adapter comprises a distal annular opening adapted to fit around a neck of the vial, and a proximal annular opening extending in an opposite direction from a transverse wall. The transverse wall supports a filling needle having a distal end extending from the distal side of the transverse wall adapted for insertion into a vial septum. The filling needle has a proximal end opening on the proximal side of the transverse wall into a medicament compartment. The medicament compartment has a side wall surrounding the opening and a septum forming a proximal end wall of the medicament compartment which receives the needle of the shield assembly. The proximal annular opening has features engaging an outer surface of the shield assembly (e.g., the outer sleeve), so that when the vial adapter is engaged to the shield assembly, movement of the first shield in a proximal direction relative to the hub is prevented. In this way, the vial can be filled without triggering the release of the inner shield.

DETAILED DESCRIPTION OF THE INVENTION

As used herein, the "distal" direction is in the direction of the injection site, and the "proximal direction" is the opposite direction. The "axial" direction is along or parallel the longitudinal axis of the syringe body. The needle cannula is generally arranged axially in a syringe. "Radially" is a direction perpendicular to the axial direction. Thus, "radially inward" generally means closer to the needle. "Tube" and "tubular" generally refer to a structure having two open ends for carrying an object or substance within. This term is used broadly so that an object having a major portion which is tubular may be referred to as tubular. A tubular syringe body, for example, may refer to a syringe and an associated plunger which closes off one end of the syringe body. The accompanying figures are schematic and not to scale.

Figure 1:
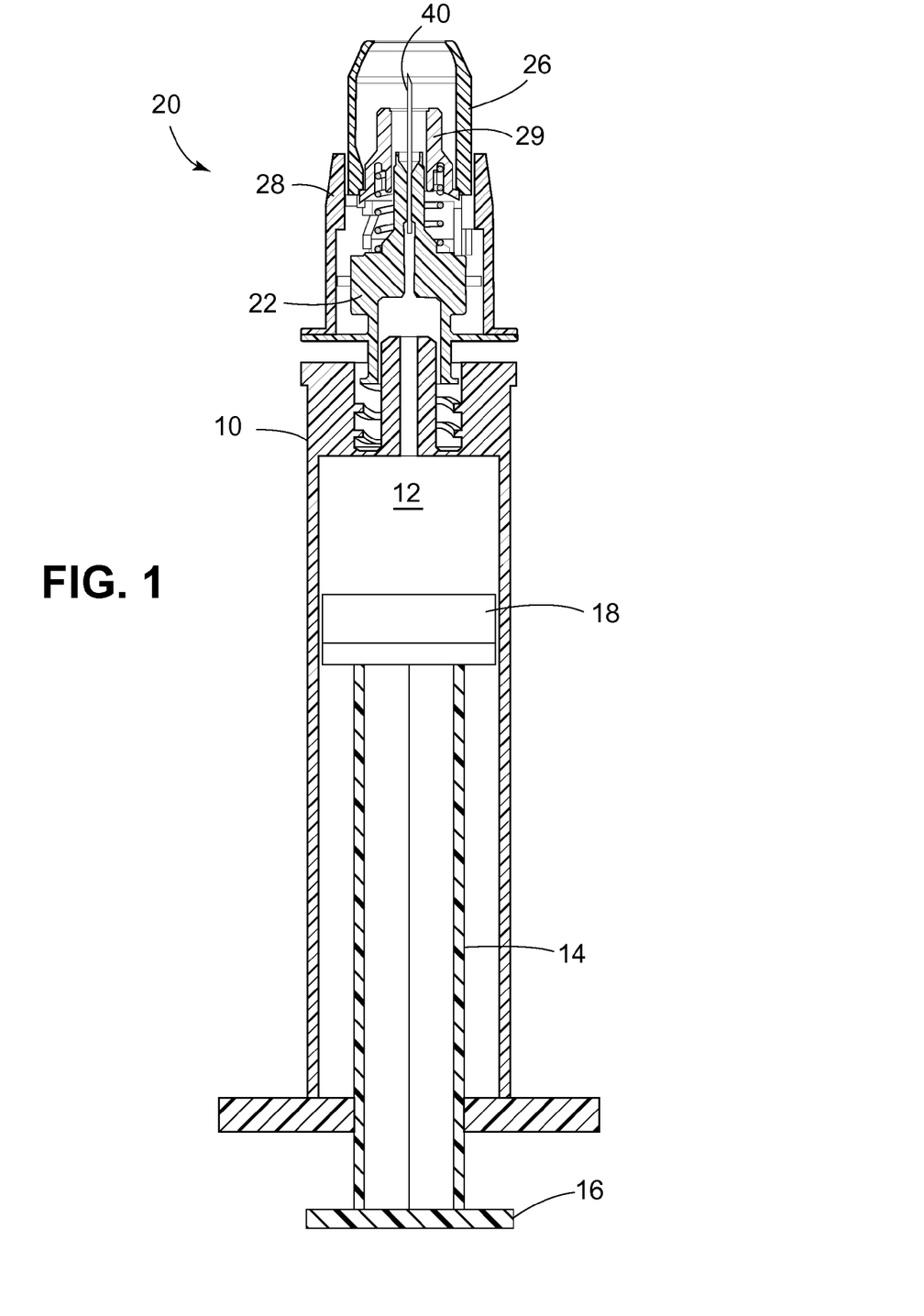
FIG. 1 is a schematic cross-sectional view of a syringe having a shield assembly removably attached according to an embodiment of the invention.

FIG. 1 shows a syringe body 10 having a medicament compartment 12 therein. A plunger 14 is positioned in the compartment with a proximal end 16 protruding from the syringe body in the form of a thumb pad, for example. Stopper 18 on the distal end of the plunger is positioned within and closes off the medicament compartment 12, such that moving the plunger distally forces medicament in the medicament compartment 12 from the distal end of the needle 40. A re-fillable syringe is characterized by a having plunger 14 that can be moved proximally to withdraw medication from a vial into compartment 12.

A shield assembly 20 is attached to the distal end of the syringe body 10. The shield assembly 20 generally includes a hub 22, a needle 40 affixed to the hub, an inner shield 29, an outer shield 26, and a sleeve 28. The inner shield 29 and outer shield 26 are formed to at least partially encircle a portion of the needle 40, and the outer shield 26 is located radially outward of the inner shield 29 and the needle 40. The shield assembly 20 may be adapted for user attachment to the syringe body 10 as shown in FIG. 1 and FIG. 2.

Figure 2:
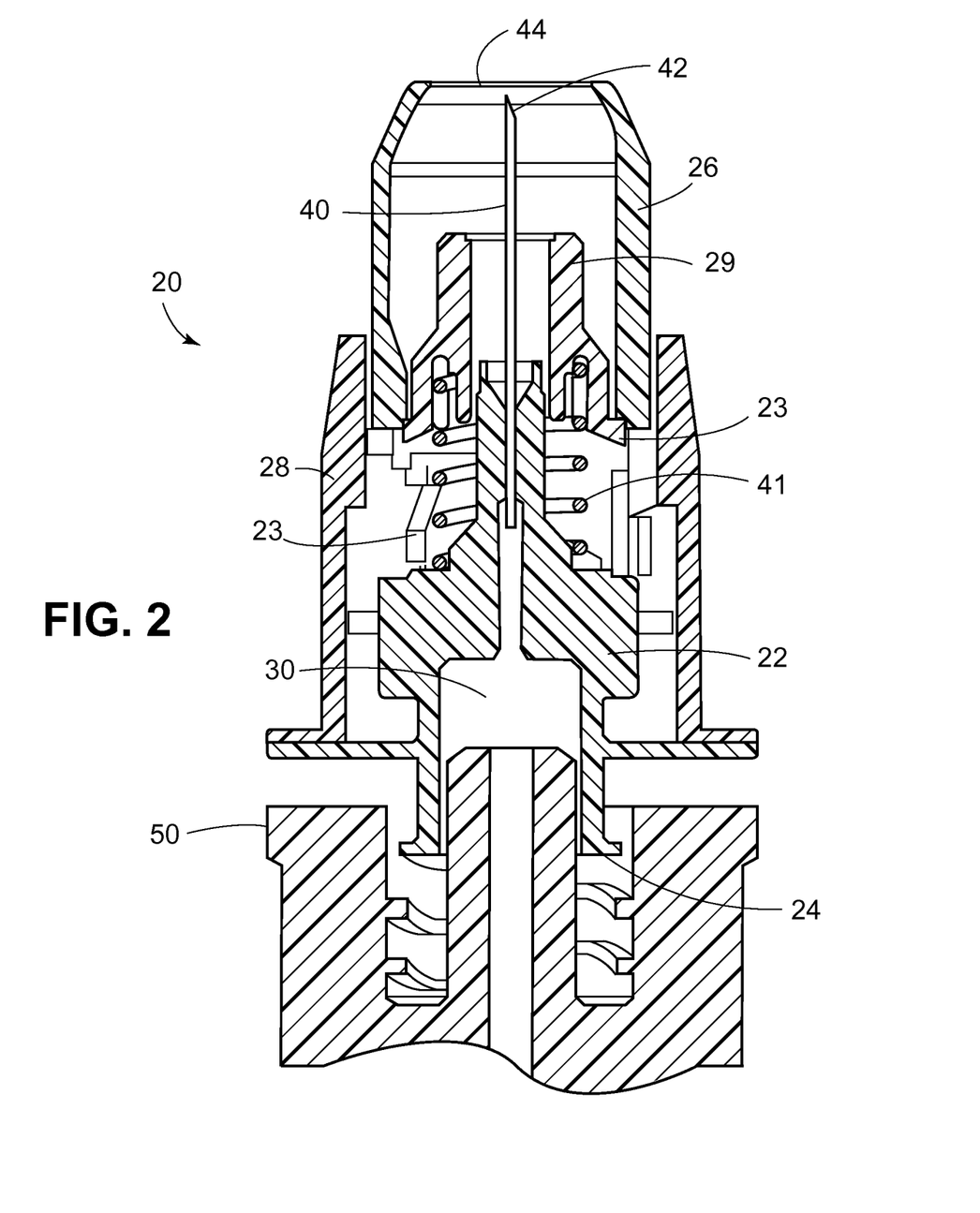
FIG. 2 is a detail of a shield assembly according to FIG. 1.

FIG. 2 depicts a detail of a shield assembly adapted to be attached to a syringe body by a user. In the state shown in FIG. 1 and FIG. 2, the shield assembly 20 is not fully attached to the syringe body. In the embodiment of FIG. 2, hub 22 is provided with a locking member 24 on the proximal end of the hub for engaging a mating member on the distal end 50 of a syringe body 10. The connection between the hub and the syringe body may be a "luer-style" connection. As used herein a "luer-style" connection refers to any coaxial overlapping connection between the hub and the syringe body characterized by a standard mating conical taper, including a "luer-lock" connection, having flanges on the hub which lock in a collar on the syringe body, a "luer-slip" connection in which the hub is pressure-mated to the syringe body without a locking member, and a "luer-snap" connection, such as disclosed U.S. Pat. No. 8,012,132 to Lunn et al., which is incorporated by reference for the purposes of describing many types of connections of a hub to a syringe body.

The needle cannula 40 is fixed to the hub and extends distally from the distal side of the hub. The distal side 42 of the needle, also sometimes referred to herein as the "patient side," is the end that is inserted into the patient. Opposite the distal end, the proximal end of the needle is located within the hub 22 having an opening adapted for receiving a fluid. In the embodiment shown, the proximal end of the needle is positioned in the interior of the hub, at one end of cavity 30 within the hub. This end is generally not honed to a point, because it is not required to pierce a septum of a medication compartment, as in a medication pen. The cavity 30 in turn accesses an opening on the distal end 50 of the syringe body. This structure is distinguished from a medication pen configuration having a filler needle protruding from the hub into the medication compartment of the injection device.

Figure 3:
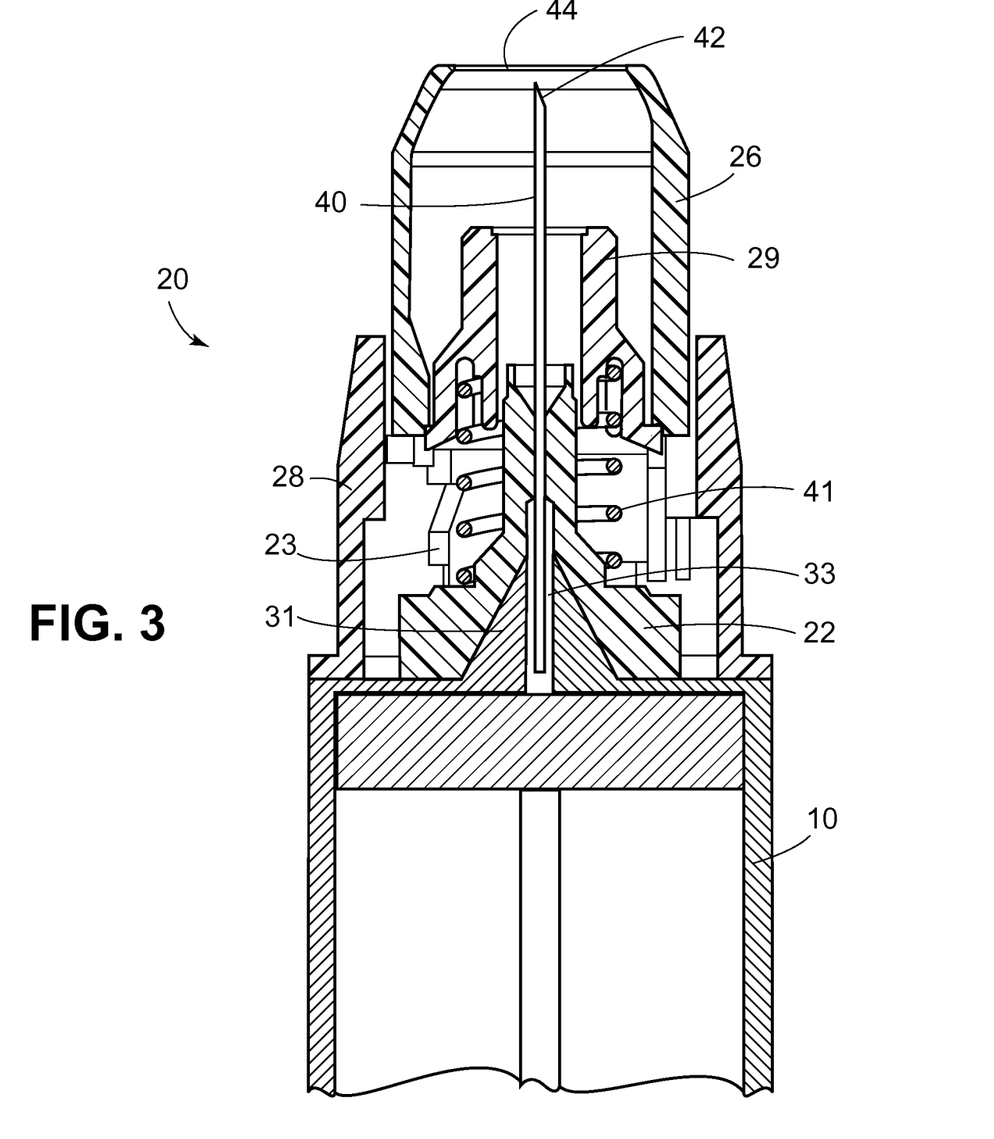
FIG. 3 is a cross-sectional schematic view of a shield assembly attached to an integral syringe body according to another embodiment of the invention.

FIG. 3 represents another embodiment of the invention, wherein shield assembly 20 is adapted for attachment to an integrally formed syringe body 10. The syringe body has a tip 31 with a tapered surface for receiving the hub 22 of the needle assembly so that the proximal end of the assembly 20, meets the distal end of the syringe body. The corresponding surfaces on the hub and syringe body may be pre-assembled and affixed to one another using adhesive, welding, shrink fitting, or other technique known in the manufacturing art. Typically, the components of shield assembly are injection molded polypropylene, apart from the cannula and springs, which are stainless steel. To assemble the parts, the shield assembly may be constructed with the needle separately and then installed on the syringe body 10, with adhesive applied in the interface area 33 to secure the cannula in the syringe body.

Figure 11:
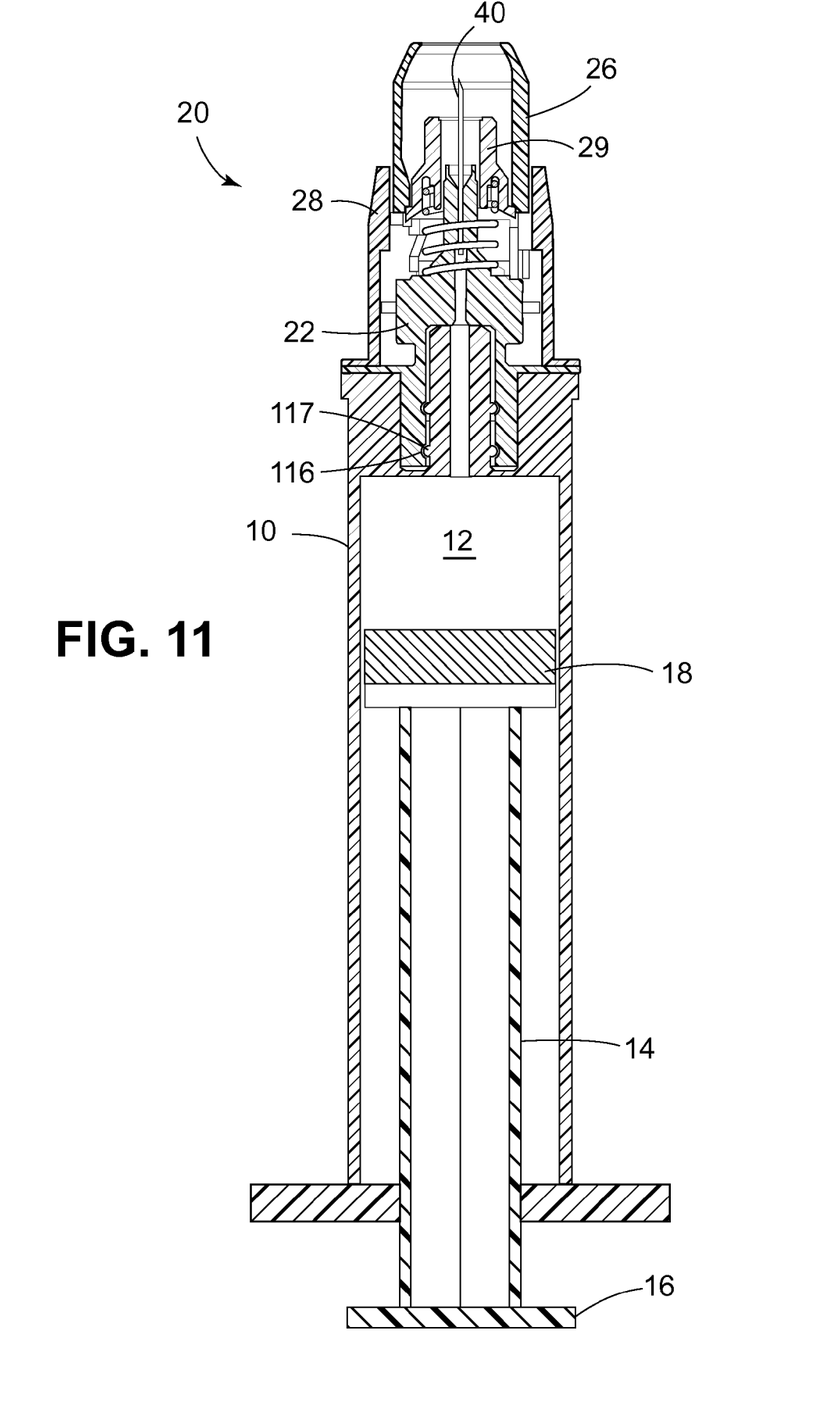
FIG. 11 is a schematic cross-sectional view of a syringe having a snap-fit hub with a needle assembly according to another embodiment of the invention.

A snap-fit embodiment is depicted in FIG. 11, wherein the hub is adapted to be installed in an opening on the syringe body. Generally, the hub is pre-assembled with the syringe body and is not removed by the user during ordinary use. Features on the proximal end of the shield assembly 20 are provided to engage corresponding features on the syringe body 10. In the depicted embodiment, a protuberance 117 around the circumference of the distal end of the syringe body 10, mates with a groove 116 on a radially inward surface of the hub 22 in a snap fit engagement. Alternatively, a groove or like element may be provided on the syringe body 10 for mating with the outer sleeve 28, or the attaching elements may be reversed. The snap fit may be made permanent by welding, adhesive, heat staking or like methods known in the art.

Returning to the cross sectional view of FIG. 2, shield assembly 20 is depicted in an initial state according to an embodiment of the invention, i.e., prior to use. In this view, the shield assembly 20 comprises an outer shield 26 that extends beyond the distal tip 42 of the needle cannula in the initial state. The outer shield prevents accidental needlestick injury prior to syringe use. It is preferred that the outer shield 26 be releasably retained in the first, initial position in which the distal end of the needle is covered by the outer shield 26. For this purpose, detents 76 on outer shield 26 (shown in FIG. 7) may cooperate with recesses provided on the outer sleeve 28. Alternatively, the elements could be reversed or a similar arrangement for releasably retaining the outer shield in the first position could be adapted by a person of ordinary skill in the art. The outer shield 26 may be made transparent to facilitate administering an injection.

It is further preferred that the inner shield 29 be releasably retained in the initial position, with the distal end of the needle protruding from the distal end of the inner shield. In this way, the distal end of the needle may be made visible for inspection in the initial state (if the outer shield is transparent, for example). For this purpose, a releasable retaining feature between the outer shield and the inner shield holds inner shield 29 against the bias of spring 41 and prevents distal movement of the inner shield 29 until the retaining feature is released by proximal movement of the outer shield 26 into the sleeve 28. The outer shield has an opening 44 on the distal end through which the needle 40 protrudes when the outer shield is moved proximally During an injection, the outer shield 26 is pushed into sleeve 28, triggering the release of inner shield 29 and upon withdrawal of the device from the patient's tissue, the inner shield 29 fully extends through the opening on the distal end of the outer shield into a locked position under bias of the spring 41. In the after-use position, the inner shield 29 extends beyond the cannula tip, guarding the contaminated tip against accidental needlestick.

Figures 7, 9:
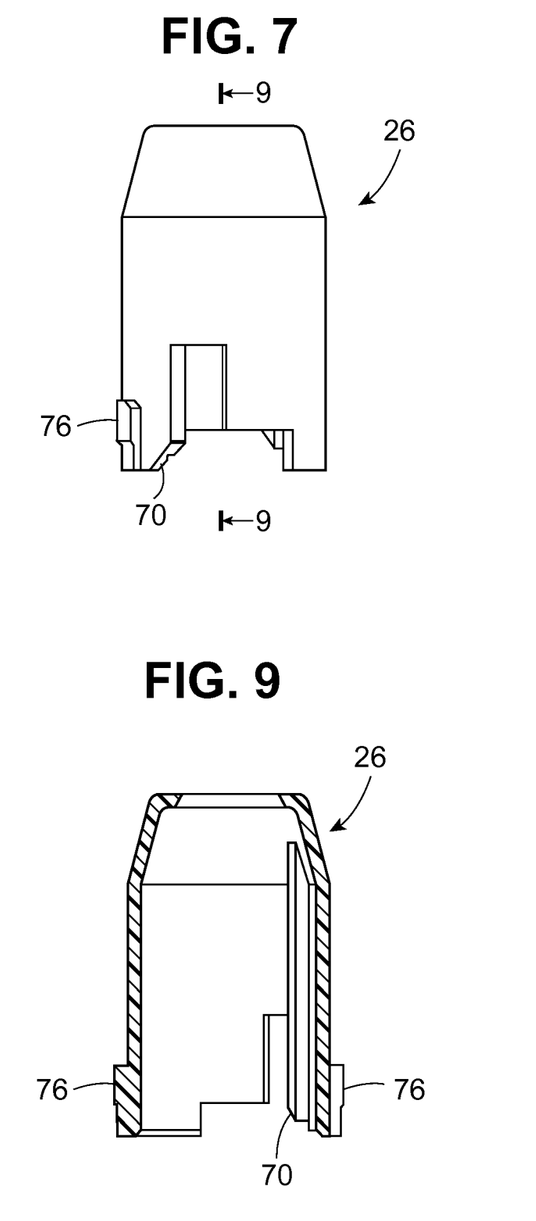
FIG. 7 is a detail of the outer shield adapted for rotating engagement with the inner shield according to an embodiment of the invention.
FIG. 9 is a cross sectional view of the outer shield according to the embodiment of FIG. 7.

The releasable retaining feature holding the inner shield in the first position may be embodied in different ways. In a preferred embodiment, proximal movement of the outer shield 26 causes relative rotation between the inner and the outer shield causing the inner shield to move from a retained position to a position in which the inner shield 29 may be urged distally. According to this embodiment of the invention, as depicted in FIG. 7, outer shield 26 includes detents 76, which engage grooves on an internal surface of the outer sleeve 28 (not shown). This engagement of the outer shield 26 and the outer sleeve 28 prevents rotation of the outer shield relative to the shield assembly during initial proximal movement of the outer shield 26 until detents clear the grooves.

Figure 8:
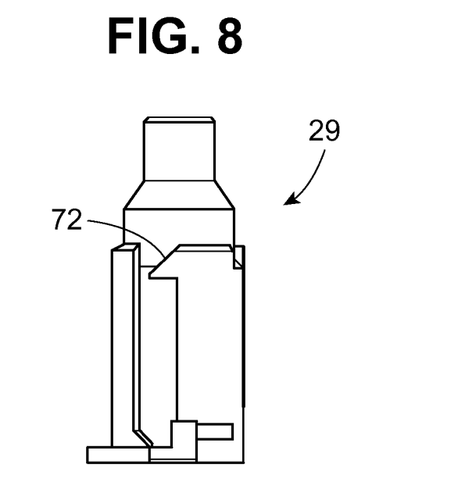
FIG. 8 is a detail of the inner shield adapted for rotating engagement with the outer shield.
Figure 10:
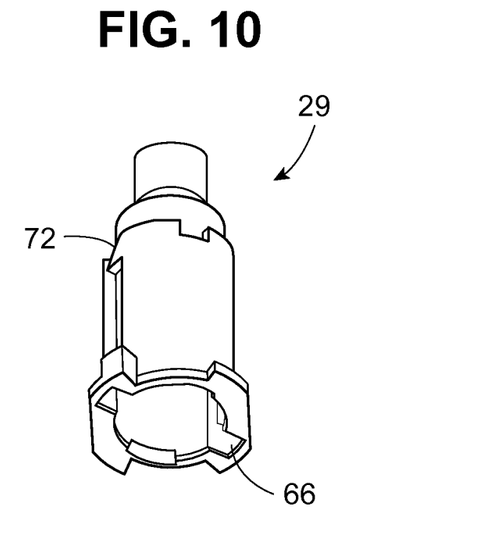
FIG. 10 is a perspective view of the inner shield according to the embodiment of FIG. 8, depicting features on the inner shield for engaging the hub of the shield assembly.

The outer shield 26 further includes a tapered surface 70, which in an initial state is aligned with a tapered receiving surface 72 formed on the inner shield 29, shown in FIG. 8. The inner and outer shields 26, 29 are configured so that with the outer shield 26 telescoped over the inner shield 29, the tapered surface 70 abuts the receiving surface 72. Further, in an initial state prior to use, protrusions on hub 22 nest within lobes 66 formed on the inner shield, which prevents rotation of the inner shield 29 relative to the shield assembly. In the initial state prior to use, due to the engagement of the outer shield and the inner shield, the bias of spring 41 maintains the outer shield in an initial state covering the distal end 42 of the needle.

Figure 5:
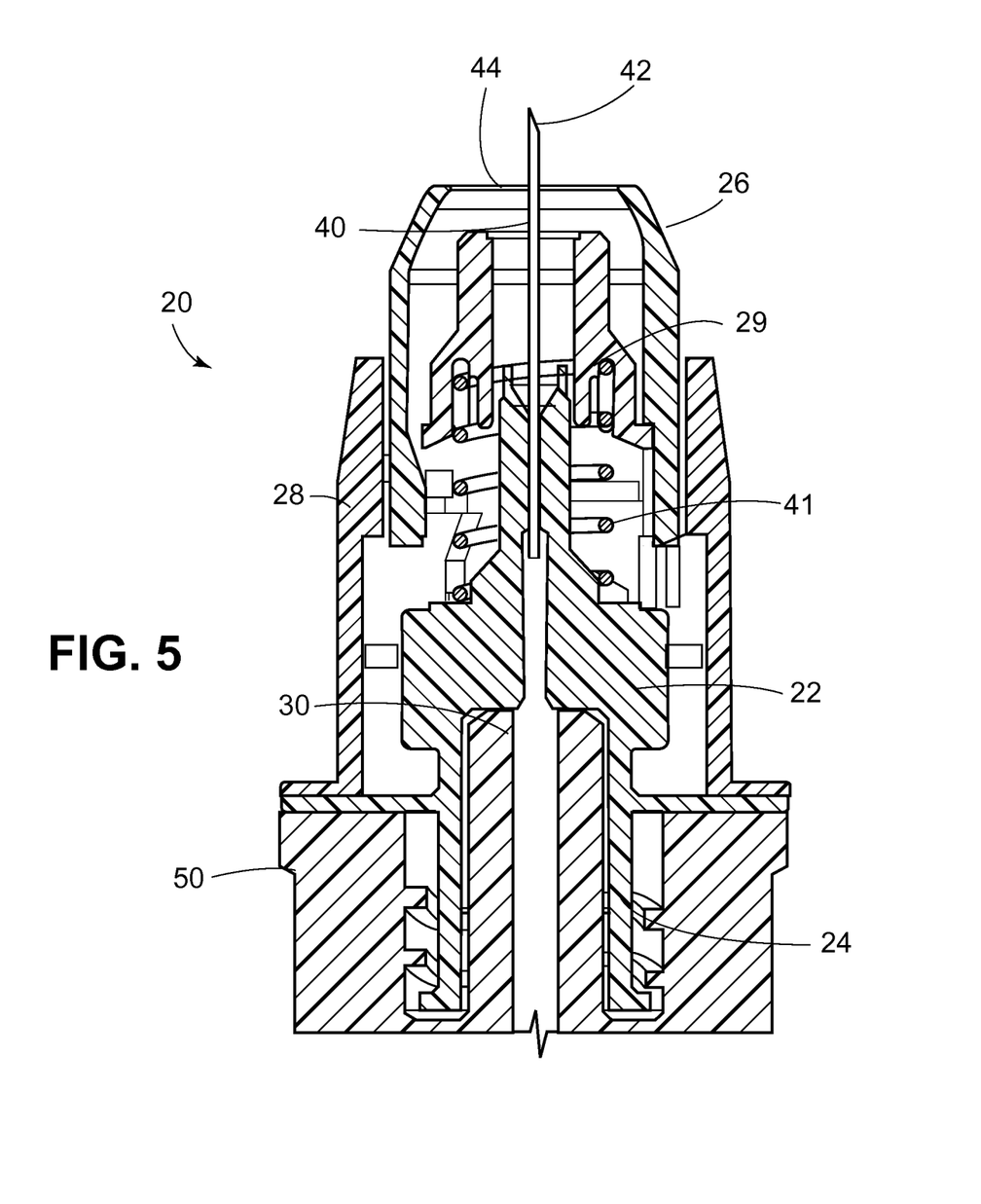
FIG. 5 is a cross-sectional detail of a shield assembly after proximal movement of the outer shield during an injection.

FIG. 5 depicts the relative position of the outer shield with respect to the shield assembly after proximal movement of the outer shield 26 relative to the inner shield 29 during an injection. Due to the engagement of the detents 76 in the grooves in the outer sleeve 28, the outer shield 26 moves axially without rotation until the detents clear the grooves. At that point, relative rotation between the shields is generated due to the contact of tapered surfaces 70, 72 against each other. As noted above, the inner shield 29 is non-rotatably held during the proximal movement of the outer shield 26 by lobes 66 which engage portions of the hub. With the inner shield 29 being held in a fixed rotational position, the tapered surface 70 is caused to rotate out of engagement with the receiving surface 72. Once the receiving surface 72 is clear, the inner shield 29 may be driven distally by the spring 41.

Figure 6:
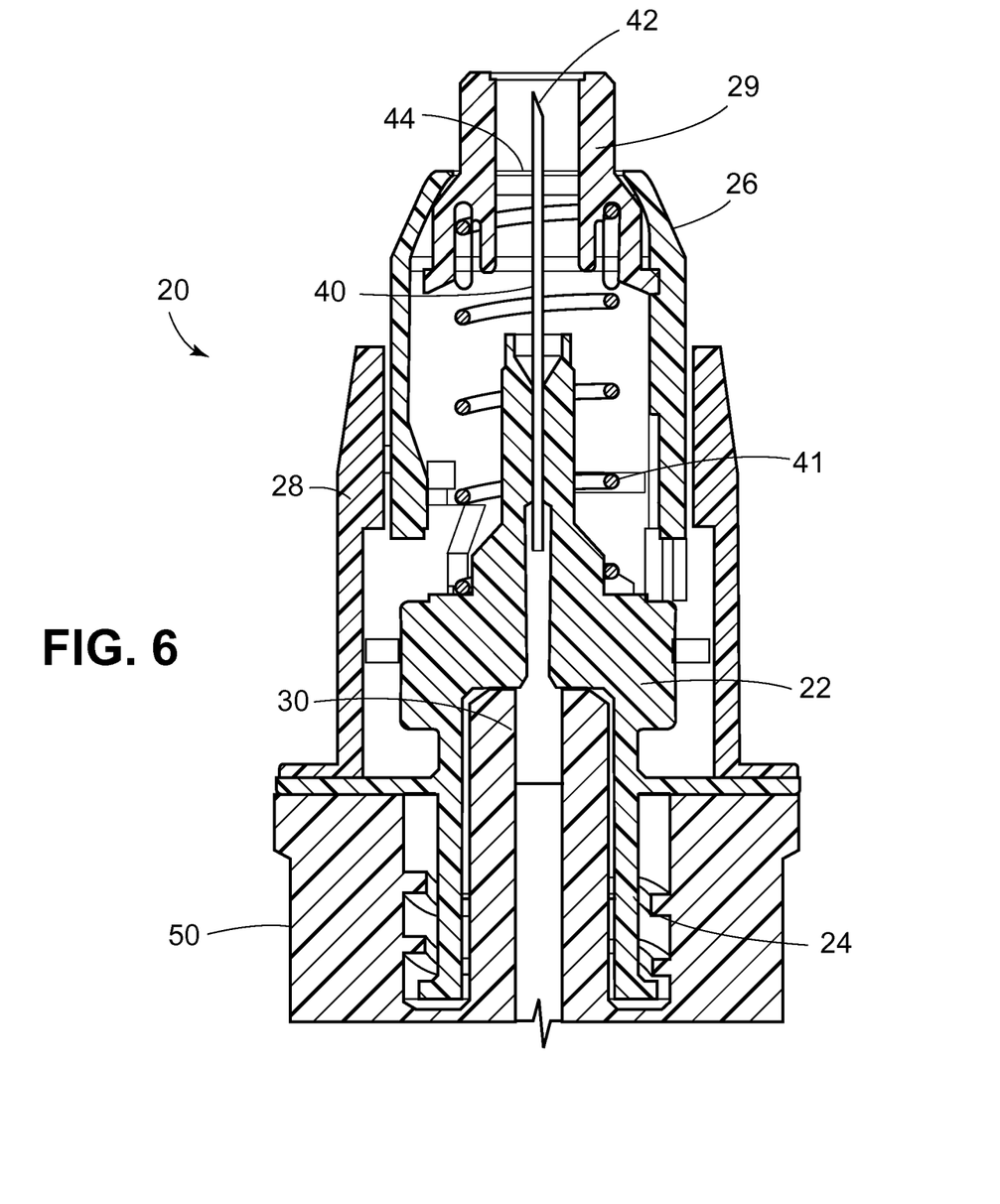
FIG. 6 is a cross-sectional detail of a shield assembly after distal movement of the inner shield after an injection.

FIG. 6 depicts a state of the shield assembly 20 after injection, with the inner shield extended over the needle cannula 40. Distal movement of the inner shield 29 may be limited by interengagement between the inner and outer shields 29, 26. In particular, the inner shield 29 may be provided with a reduced diameter portion sized to pass through the opening 44. A shoulder formed on the inner shield 29 may be formed with a larger diameter than the opening 44, thus limiting passage of the first shield 29 through the opening 44. As shown in FIG. 6, the inter-engagement between the outer shield 26 and the shoulder of the inner shield 29 limits distal movement of the inner shield 29.

A locking arrangement may also be provided to limit proximal movement of the inner shield 29 once in the final shielding position where the inner shield 29 covers the distal end of the needle 40. For this purpose, the first shield 29 may be provided with an inwardly deflectable locking arm formed to be biased against a portion of the hub 22 in the final shielding position of the inner shield 29.

Other configurations of a dual shield mechanism may be adapted from among dual shield assemblies that have been used with a pen injector, such as disclosed in U.S. Patent Application Publication Nos. 2011/0288491 and 2011/0257603, which are incorporated by reference.

Figure 4:
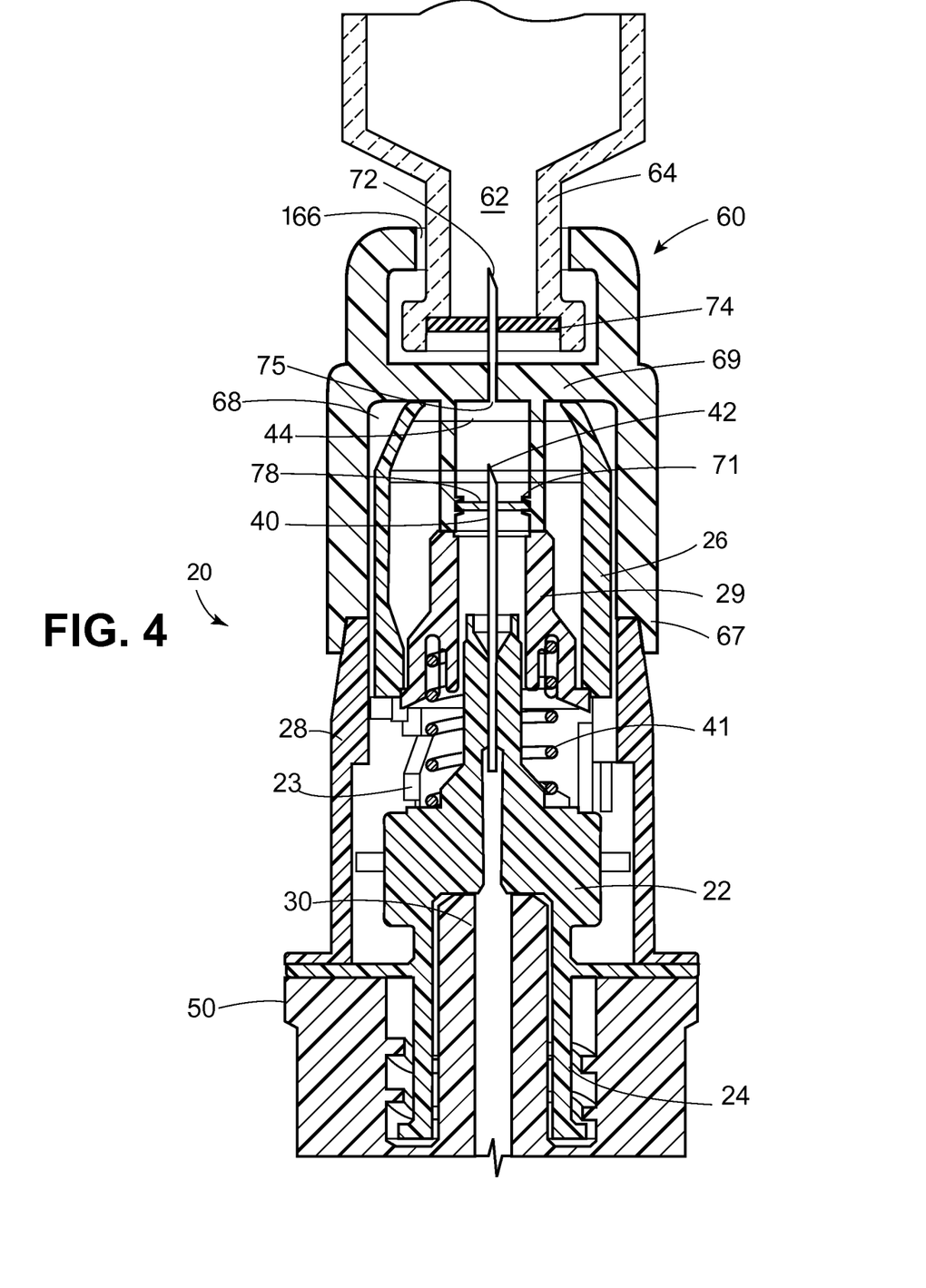
FIG. 4 is a cross-sectional view of a dual-shield syringe according to the invention with a vial adapter attached between the shield assembly and a vial for filling the syringe.

In another aspect, the invention incorporates a vial adapter for use with a shielded syringe which allows filling a dual shielded syringe from a vial without activating the shield. As shown in FIG. 4, a vial adapter 60 according to one embodiment of the invention permits the syringe to be filled from a vial 62 without triggering the releasable mechanism of the dual shield assembly 20. In this configuration, the vial adapter 60 is adapted to snap fit around a vial neck 64 by way of a distal annular opening 166. A proximal annular opening 68 extends in an opposite longitudinal direction from a transverse wall 69. The proximal end 67 of the proximal opening of the vial adapter positions against the outer sleeve 28 of the shield assembly 20 without triggering the automatic shield mechanism because needle 40 can access medicament without moving outer shield 26. For this purpose, the proximal end 67 of the adapter 60 may be provided with features which engage mating features on the outer sleeve 28 of the shield assembly, as shown in FIG. 4. In embodiments, the vial adapter may abut an extension on the distal end 50 of the syringe body, the critical feature being that movement of the outer shield 26 that would trigger the passive shielding mechanism is prevented.

In the embodiment shown in FIG. 4, the transverse wall 69 of the vial adapter 60 supports a needle 72 having a distal end extending from the distal side of the transverse wall 69 which can be inserted into a vial septum 74. An opening 75 opens onto the proximal side of the transverse wall 69. A Side wall extends from the transverse wall 69 and surrounds the opening 75 forming a medicament compartment. The medicament compartment has a septum 78 forming a proximal end wall of the compartment, while the transverse wall 69 of the vial adapter forms the opposite end wall of the medicament compartment.

When the proximal end 67 of annular opening 68 is positioned on the shield assembly 20, the medicament compartment fits inside the opening 44 of the outer shield 26 of the shield assembly. The medicament compartment is sized so as to approach the distal end of the inner shield, with sufficient distal end of the needle cannula exposed to pierce septum 78 and access the medicament compartment 76. Thus, the needle 40 of the shield assembly 20 draws fluid into the syringe from the medication compartment while movement of the outer shield 26 in a proximal direction relative to the hub are prevented by the engagement of the proximal end of the vial adapter 60 with the sleeve 28 during the filling process. In this way, the syringe can be filled from the vial without triggering the shield.

The vial adapter may be provided in a kit with a shield assembly, adapted for user attachment to the syringe body. In some embodiments a suitable kit may provide one vial adapter for a plurality of shield assembly devices. The user may choose to leave the vial adapter on the vial for repeated fillings.

The foregoing description of the preferred embodiments is not to be deemed limiting of the invention defined by the following claims. The foregoing description should provide the artisan of ordinary skill with sufficient information to practice variants of the embodiments described. Features and improvements described in the dependent claims may be combined with other embodiments, with other independent claims, or with other dependent claims without departing from the scope of the invention.

What is claimed is:

1. A dual shielded re-fillable syringe with vial adapter, comprising:
    a tubular syringe body having a distal end, a proximal end, and features on the distal end adapted to engage a shield assembly, the shield assembly comprising:
        a hub having features on a proximal end thereof for engaging the distal end of the syringe body;
        a needle fixed to the hub having a distal end extending from the hub and a proximal end in the interior of the hub which does not extend from the hub;
        an inner shield having a tubular body at least partially encircling the needle;
        an outer shield having a tubular body radially outward of the inner shield covering the needle in an initial position prior to injection and having an opening on the distal end thereof which receives the distal end of the inner shield;
        a spring disposed to urge the inner shield distally through the opening in the outer shield towards the distal end of the needle;
        an outer sleeve at least partially encircling the inner and outer shields; and
        a releasable retaining feature retaining the inner shield in an initial position, wherein a predetermined proximal movement of the outer shield relative to the hub and into the outer sleeve during an injection releases the inner shield to urge the inner shield under the bias of the spring to a position covering the distal end of the needle; and a vial adapter, having:
    a distal annular opening adapted to fit around the neck of a vial and a proximal annular opening extending opposite the distal annular opening from a transverse wall;
    the transverse wall supporting a filler needle extending distally from the transverse wall adapted for insertion into a vial septum, and having a proximal end with an opening onto the proximal side of the transverse wall;
    a medicament compartment having a side wall surrounding the opening on the proximal end of the filler needle and a septum forming a proximal end wall of the medicament compartment, said septum receiving the needle of the shield assembly; and wherein
    the proximal annular opening engages the outer sleeve of the shield assembly so that when the vial adapter is engaged to the shield assembly, the medicament compartment is positioned in the opening on the distal end of the outer shield, the needle pierces the septum of the medicament compartment, and movement of the outer shield in a proximal direction relative to the hub is prevented.

2. The dual shielded syringe according to claim 1, wherein the syringe body and the hub are connected by a luer-style tapered connection.

3. The dual shielded syringe according to claim 1, wherein the syringe body is integrally molded with the hub.

4. The dual shielded syringe according to claim 1, wherein the shield assembly is snap fit into a distal opening on the syringe barrel.

5. The dual shielded syringe according to claim 1, wherein the releasable retaining feature comprises a tapered surface on the outer shield engaging a corresponding tapered surface on the inner shield causing rotation of the outer shield relative to the inner shield when the outer shield is moved proximally, which rotation causes the inner shield to be released from the initial position.

6. The dual shield syringe according to claim 5, wherein the outer shield is constrained to move axially, without rotation, for a predetermined amount of proximal movement of the outer shield prior to said rotation of the outer shield being initiated.

7. The dual shielded syringe according to claim 6, wherein the inner shield engages the hub to prevent rotation of the inner shield when the outer shield is caused to rotate.

* * * * *